United States Patent [19]

Corcoran et al.

[11] Patent Number: 5,368,857
[45] Date of Patent: Nov. 29, 1994

[54] CERAMIDE COSMETIC COMPOSITIONS

[75] Inventors: Cathleen Corcoran, Bridgeport; Jason Hendry, Cheshire, both of Conn.

[73] Assignee: Elizabeth Arden Company, Division of Conopco, Inc., New York, N.Y.

[21] Appl. No.: 153,013

[22] Filed: Nov. 15, 1993

[51] Int. Cl.$^5$ ................................................. A61K 7/48
[52] U.S. Cl. .................................... 424/401; 514/844; 514/847
[58] Field of Search ................. 424/401; 514/844, 847

[56] References Cited

PUBLICATIONS

JP 63-192703, Abstract (1988).

Primary Examiner—Gollamudi S. Kishore
Assistant Examiner—Jyothsna Venkat
Attorney, Agent, or Firm—Milton L. Honig

[57] ABSTRACT

A cosmetic composition is provided wherein a phytosphingosine-containing ceramide is stably suspended within a $C_6$–$C_{100}$ ester base functioning as a pharmaceutically acceptable carrier and the ceramide is solubilized by a glycerol $C_8$–$C_{22}$ mono fatty acid ester.

3 Claims, No Drawings

CERAMIDE COSMETIC COMPOSITIONS

BACKGROUND OF THE INVENTION

1. Field of the Invention

The invention concerns a cosmetic composition wherein ceramides are stably incorporated into a non-separating product.

2. The Related Art

Ceramides are an important group of lipids, members of which are found in the epidermis of mammals. Skin ceramides are believed to play an important role in the water permeability properties of the skin, providing an epidermal water-barrier which functions to give increased strength to the skin structure and to decrease water loss and so improve the condition of the skin.

Ceramides are N-acylated sphingosine bases. Sphingosine bases are of variable chain length and have the general formula (1):

$$CH_3(CH_2)_x ACHOHCH(NH_2)CH_2OH \qquad (1)$$

where A is $-CH=CH-$ (sphingosine), $-CH_2\text{-}CHOH-$ (phytosphingosine) or $-CH_2CH_2-$ (dihydrosphingosine), and where x is generally in the broad range 7 to 27, more typically in the range 10 to 16. It should be noted that sphingosines contain asymmetric carbon atoms and so various stereoisomers are possible. Sphingosine/ceramides from especially mammalian sources are all the D-erythro isomer and phytosphingosine/phytoceramides the D-D-erythro isomer. Seven distinguishable groups of ceramides have been identified in pig and human epidermis. Each group consists of molecules of varying fatty acid chain length. The structures of typical skin ceramides are described in the paper entitled "Ceramides of Pig Epidermis: Structure Determination" by P. W. Wertz and T. T. Downing in Journal of Lipid Research, Col. 24, 1983, pages 759–765.

Problems have been encountered when phytosphingosine-containing ceramides are incorporated into pharmaceutically acceptable carrier systems. These ceramides are extremely insoluble, especially in ester type carriers and where single phase transparent formulas are sought.

Accordingly, it is an object of the present invention to provide a phytosphingosine-containing ceramide composition wherein all components including the ceramide are dissolved or at least stably suspended. Another object of the present invention is to provide a phytosphingosine-containing ceramide cosmetic composition which is a clear (transparent) formula.

These and other objects of the present invention will become more apparent from consideration of the following summary and detailed description.

SUMMARY OF THE INVENTION

A cosmetic composition is provided which includes:
(i) from about 0.00001 to 2% by weight of a phytosphingosine-containing ceramide having the general structure (2)

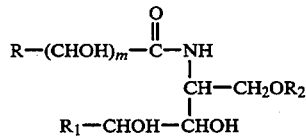

wherein

R represents a linear or branched, saturated or unsaturated, hydroxylated or non-hydroxylated aliphatic hydrocarbon group having from 1 to 49 carbon atoms or a subgroup (3):

$$Y-O-(C_aH_b)-$$

$R_1$ represents a linear or branched, saturated or unsaturated, hydroxylated or non-hydroxylated aliphatic hydrocarbon group having from 8 to 28 carbon atoms;

$R_2$ represents H, a phosphate, a sulphate or a sugar:
 a is an integer of from 7 to 50
 b is an integer of from 10 to 100
 m is 0 or 1

Y represents H or a residue of a $C_{14}-C_{22}$ fatty acid having the general structure (4):

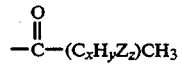

where
 z is $-OH$ or an epoxy oxygen
 x is an integer of from 12 to 20
 y is an integer of from 20 to 40
 z is 0 or an integer of from 1 to 4; and (ii) from about 30 to about 95% by weight of a $C_6-C_{100}$ ester base functioning as a pharmaceutically acceptable carrier; and (iii) from about 0.1 to about 20% by weight of a glycerol $C_8-C_{22}$ mono fatty acid ester as a coupling agent for solubilizing the ceramide within the base.

DETAILED DESCRIPTION

Now it has been discovered that phytosphingosine-containing ceramides can be solubilized within a $C_6-C_{100}$ ester base carrier through use of a coupling agent. The coupling agent is a glycerol $C_8-C_{22}$ mono fatty acid ester.

The phytosphingosine-containing ceramide has the general structure (2):

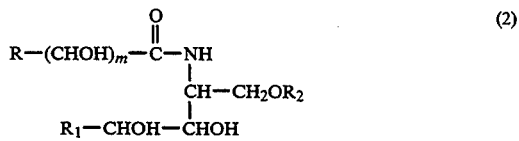

wherein

R represents a linear or branched saturated or unsaturated, hydroxylated or non-hydroxylated aliphatic hydrocarbon group having from 1 to 49 carbon atoms or a subgroup (3):

$$Y-O-(C_aH_b)- \qquad (3)$$

$R_1$ represents a linear or branched, saturated or unsaturated, hydroxylated or non-hydroxylated aliphatic hydrocarbon group having from 8 to 28 carbon atoms;

$R_2$ represents H, a phosphate, a sulphate or a sugar:
 a is an integer of from 7 to 50
 b is an integer of from 10 to 100
 m is 0 or 1

Y represents H or a residue of a $C_{14}-C_{22}$ fatty acid having the general structure (4):

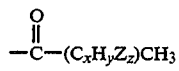

where
z is —OH or an epoxy oxygen
x is an integer of from 12 to 20
y is an integer of from 20 to 40
z is 0 or an integer of from 1 to 4.

With reference to structure (2), the group R preferably represents an aliphatic hydrocarbon group having from 12 to 30 carbon atoms or the group $Y-O-(C_aH_b)-$; while the group $R_1$ preferably represents an aliphatic hydrocarbon group having from 12 to 22 carbon atoms.

With reference to structure (3), the value of "a" is preferably an integer of from 24 to 30 and the value of "b" is preferably an integer of from 44 to 60.

Also, with reference to structure (3), the group Y preferably represents a straight chain saturated $C_{16}$–$C_{18}$, fatty acid residue or a straight chain all cis n-6,9 di-unsaturated $C_{16}$–$C_{18}$ fatty acid residue.

Specific examples of these phytosphingosine-containing ceramides are those having the structures (5) to (17):

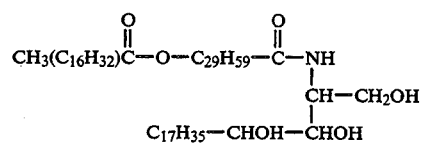

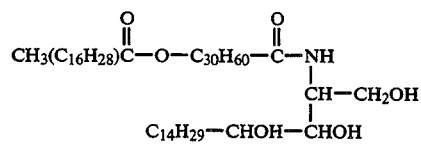

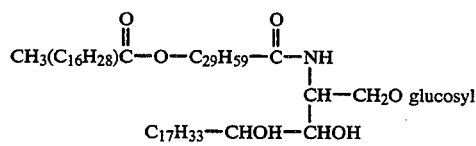

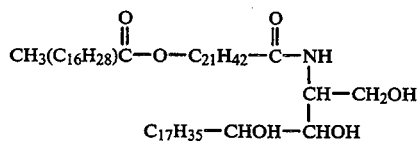

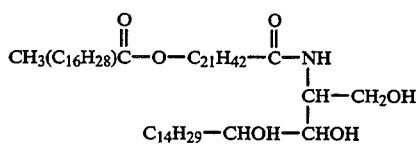

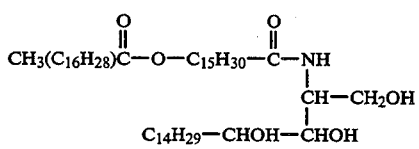

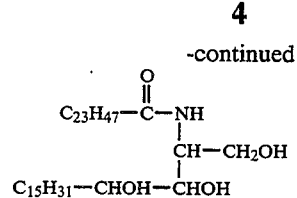

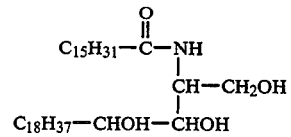

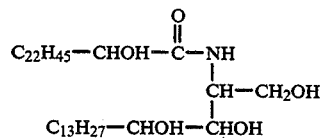

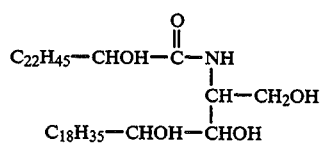

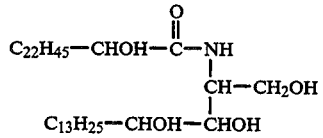

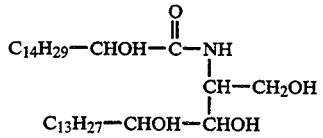

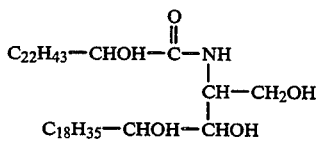

The amount of the phytosphingosine-containing ceramide present in the composition according to the invention is from 0.00001 to 2%, preferably from 0.001 to 1%, optimally from 0.01 to 0.1% by weight.

The most preferred ceramide is Ceramide 3 referred to as N-stearoyl-phytosphingosine.

A second important component of cosmetic compositions according to the present invention is that of a $C_6$–$C_{100}$ ester base functioning as a pharmaceutically acceptable carrier for the ceramides. Amounts of the ester base may range from 30 to 95%, preferably from 40 to 80%, optimally from 50 to 70% by weight.

In order to solubilize the ceramides into the ester base, it has been found necessary to utilize a glycerol $C_8$–$C_{22}$ mono fatty acid ester. Amounts of the solubilizer will range from about 0.1 to about 20%, preferably from about 0.5 to 10%, optimally from about 1 to 5% by weight. Illustrative solubilizers include glycerol monoisostearate, glycerol monobehenate and glycerol monopalmitate. Most preferred, however, is glycerol monoisostearate commercially available from the Scher Chemical Corp. as Schercemol GMIS.

Among the suitable materials for the $C_6$–$C_{100}$ ester base carrier are the following:

(1) from about 1 to about 90% of $C_7-C_{60}$ neoalkanol ester;
(2) from about 1 to about 90% of $C_{12}-C_{40}$ fatty glyceride ester alkoxylated with from 1 to 100 moles $C_2-C_3$ alkylene oxide per mole of glyceride;
(3) from about 1 to about 90% of a polyglycerol $C_8-C_{22}$ mono or di-fatty acid ester;
(4) from about 1 to about 90% of a $C_8-C_{22}$ alkanol ester of a $C_8-C_{22}$ fatty acid.

The $C_7-C_{60}$ neoalkanol ester will normally be present in an amount from 1 to 90%, preferably from 20 to 75%, optimally from 30 to 50% by weight. Illustrative of this category are esters formed from the reaction between $C_1-C_{22}$ alkanoic acid with either neopentyl alcohol, neopentyl glycol, 2-butyl-2-ethyl-1,3-propane diol, 2,2,4-trimethyl-1,3-pentane diol, trimethylol propane, pentaerythritol, di-trimethylol propane, di-pentaerythritol or pentaerythritol-trimethylol propane dimers. Examples include isostearyl neopentanoate, palmityl neopentanoate, tetraoctylpentaerythritol and diisopropyl neopentanoate. Most preferred is isostearyl neopentanoate.

The $C_{12}-C_{14}$ fatty glyceride ester alkoxylate will include from 1 to 100 moles alkylene oxide per mole of glyceride, preferably from 4 to 20 moles alkylene oxide per mole of glyceride. The preferred alkylene oxides are ethylene oxide and propylene oxide. Amounts of this ester may range from 1 to 90%, preferably from 5 to 50%, optimally from 10 to 20% by weight of the composition. Illustrative of this category are PEG-6 caprylic/capric glyceride and PEG-8 caprylic/capric glyceride each of which are polyethylene glycol derivatives of a mixture of mono, di and triglycerides of caprylic and capric acids with a respective 6 and 8 moles of ethylene oxide. The higher alkoxylated ester is available from Gattefosse sold under the trademark of Labrasol.

Advantageously, the ester base of the present composition may further include a polyglycerol $C_8-C_{22}$ fatty acid ester. Amounts of this ester may range from 1 to 50%, preferably from 5 to 25%, optimally from 10 to 20% by weight of the composition. Illustrative of this category are polyglycerol-3 beeswax, polyglycerol-4 cocoate, polyglycerol-10 decalinoleate, polyglycerol-10 decaoleate, polyglycerol-7 decastearate, polyglycerol-2 diisostearate, polyglycerol-3 diisostearate, polyglycerol-7 diisostearate, polyglycerol-2 dioleate, polyglycerol-3 dioleate, polyglycerol-6 dioleate, polyglycerol-10 dioleate, polyglycerol-3 distearate, polyglycerol-6 distearate, polyglycerol-10 distearate, polyglycerol-10 heptaoleate, polyglycerol-10 heptastearate, polyglycerol-6 hexaoleate, polyglycerol-2 isostearate, polyglycerol-4 isostearate, polyglycerol-6 isostearate, polyglycerol-10 laurate, polyglycerol-10 myristate, polyglycerol-2 oleate, polyglycerol-3 oleate, polyglycerol-4 oleate, polyglycerol-6 oleate, polyglycerol-8 oleate, polyglycerol-10 oleate and combinations thereof. Most preferred is polyglycerol-6 dioleate which is a diester of oleic acid and a glycerin polymer containing an average of 6 glycerin units, available from Gattefosse under the trademark Plurol Oleique WL 1173.

A still further component of the ester base may be simple $C_3-C_{22}$ alkanol esters of $C_8-C_{22}$ alkanoic acids. Amounts of this material may range from 1 to about 50%, preferably from 5 to 30%, optimally from 10 to 20% by weight of the cosmetic composition. Illustrative of this category are cetyl octanoate, lauryl pentanoate, palmityl palmitoate, isostearyl decanoate, oleyl heptanoate and combinations thereof. Most preferred are cetyl octanoate available under the trademark Trivent OC-16.

Compositions of the present invention are preferably anhydrous (less than 2% but preferably less than 0.5% water) but may also be aqueous. When water is present, the product form may be as an emulsion in the form of a lotion or cream.

Other types of pharmaceutically acceptable carriers such as silicone oils may also be included in the cosmetic compositions of the present invention. Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients.

Silicones may be present in amounts ranging from about 1 to about 50%, preferably from about 2 to about 25%, optimally between about 10 and 20% by weight.

Fatty alcohols and fatty acids having from 10 to 20 carbon atoms may also be included in compositions of the present invention. Especially preferred are such compounds as cetyl, myristyl, palmityl, isostearyl and stearyl alcohols and acids.

Besides ceramides the compositions of this invention may also include a wide variety of α-hydroxy carboxylic acids. Suitable examples include:
α-hydroxyethanoic acid α-hydroxypropanoic acid
α-hydroxyhexanoic acid
α-hydroxyoctanoic acid
α-hydroxydecanoic acid
α-hydroxydodecanoic acid
α-hydroxytetradecanoic acid
α-hydroxyhexadecanoic acid
α-hydroxyoctadecanoic acid
α-hydroxyeicosanoic acid
α-hydroxydocosanoic acid
α-hydroxyhexacosanoic acid, and
α-hydroxyoctacosanoic acid Particularly preferred from the above list are α-hydroxyethanoic acid (commonly known as glycolic acid), α-hydroxypropanoic acid (commonly known as lactic acid) and α-hydroxyoctanoic acid (commonly known as α-hydroxycaprylic acid or HCA).

For purposes of this invention, the term α-hydroxy carboxylic acids are intended to include not only the acid form but also salts thereof. Typical salts are the alkalimetal, ammonium and $C_2$–$C_{30}$ ammonium salts thereof. Particularly preferred are the sodium, potassium, triethanolammonium and ammonium salts. Combinations of all the foregoing may be present in the compositions.

Amounts of the α-hydroxy carboxylic acid will range from 0.001 to 20%, preferably from 0.01 to 15%, optimally from 0.5 to 10% by weight of the cosmetic composition.

Vitamins may also be included in the compositions of the present invention. Especially preferred is vitamin A palmitate (retinyl palmitate) and vitamin E linoleate (tocopheryl linoleate). Other esters of vitamins A and E may also be utilized.

Emulsifiers may also be incorporated into cosmetic compositions of the present invention. These emulsifiers may range from 0.5 to 30%, preferably from 1 to 15%, optimally from 3 to 8% by weight. Emulsifiers may be nonionic, anionic, cationic or amphoteric in nature and combinations thereof may be employed.

Most preferred for purposes of this invention are the emulsifiers PPG-5-ceteth-20 which is a polyoxypropylene-polyoxyethylene ether of cetyl alcohol commercially available from Croda under the trademark Procetyl AWS and glycerol monoisostearate commercially available from the Scher Chemical Company under trademark Schercemol GMIS.

Another category of functional ingredient within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, proprionate salts, and a variety of quaternary ammonium compounds.

Particularly preferred preservatives are methyl paraben, propyl paraben, imidazolidinyl urea, sodium dehydroxyacetate and benzyl alcohol. Preservatives will usually be employed in amounts ranging from about 0.1% to 2% by weight of the composition.

Powders may be incorporated into the cosmetic compositions of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

The following examples will more fully illustrate selected embodiments of this invention. All parts, percentages and proportions referred to herein and in the appended claims are by weight unless otherwise indicated.

EXAMPLE 1

This example illustrates a series of cosmetic compositions according to the present invention.

TABLE I

| COMPONENT | FORMULA (WT. %) | | | |
|---|---|---|---|---|
| | 1 | 2 | 3 | 4 |
| l-Lactic Acid | 2.00 | 3.00 | 4.00 | 5.00 |
| Potassium l-Lactate | 0.93 | 1.41 | 1.88 | 2.34 |
| Isostearyl Neopentanoate | 36.50 | 35.01 | 33.54 | 32.08 |
| PEG-8 Caprylic/Capric Glycerides | 14.30 | 14.30 | 14.30 | 14.30 |
| Cetyl Octanoate | 12.75 | 12.75 | 12.75 | 12.75 |
| Polyglyceryl-6 Dioleate | 11.90 | 11.90 | 11.90 | 11.90 |
| Cyclomethicone | 10.17 | 10.17 | 10.17 | 10.17 |
| PPG-5-Ceteth-20 | 5.10 | 5.10 | 5.10 | 5.10 |
| Glyceryl Isostearate | 3.13 | 3.13 | 3.13 | 3.13 |
| Hydroxycaprylic Acid | 0.01 | 0.01 | 0.01 | 0.01 |
| Ceramide 2 | 0.10 | 0.10 | 0.10 | 0.10 |
| Ceramide 3 | 0.01 | 0.01 | 0.01 | 0.01 |
| Water | qs | qs | qs | qs |

EXAMPLE 2

This example demonstrates the effect of various glycerol esters on solubilizing Ceramide 3. The formulations tested and the stability results, i.e. clarity, are reported in Table II. Only glycerol monoisostearate provided a non-cloudy, clear composition. Other glycerol esters were ineffective in solubilizing the Ceramide 3, even at the low level of 0.01%.

TABLE II

| COMPONENT | FORMULA (WT. %) | | | | | | |
|---|---|---|---|---|---|---|---|
| | A | B | C | D | E | F | G |
| Isostearyl Neopentanoate | 96.89 | 96.89 | 96.89 | 96.89 | 96.89 | 96.89 | 96.89 |
| Ceramide 2 | 0.10 | 0.10 | 0.10 | 0.10 | 0.10 | 0.10 | 0.10 |

TABLE II-continued

| COMPONENT | FORMULA (WT. %) | | | | | | |
|---|---|---|---|---|---|---|---|
| | A | B | C | D | E | F | G |
| Ceramide 3 | 0.01 | 0.01 | 0.01 | 0.01 | 0.01 | 0.01 | 0.01 |
| Glycerol Monoisostearate | 3.0 | — | — | — | — | — | — |
| Pentaerythritol Tetraisostearate | — | 3.0 | — | — | — | — | — |
| Decaglycerol Monoisostearate | — | — | 3.0 | — | — | — | — |
| Polyglycerol Triisostearate | — | — | — | 3.0 | — | — | — |
| Polyglycerol-6-Isostearate | — | — | — | — | 3.0 | — | — |
| Triglycerol Diisostearate | — | — | — | — | — | 3.0 | — |
| Polyglycerol-3-Diisostearate | — | — | — | — | — | — | 3.0 |
| Stability: | Clear | Cloudy | Cloudy | Cloudy | Cloudy | Cloudy | Cloudy |

The foregoing examples illustrated only selected embodiments of the present invention and should be considered nonlimiting examples with variations and modifications thereof all being within the spirit and purview of this invention.

What is claimed is:

1. A cosmetic composition comprising:
   (i) from about 0.00001 to 2% by weight of a phytosphingosine-containing ceramide having structure:

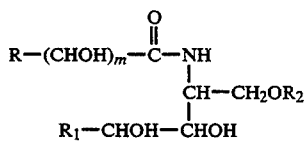

wherein
   R represents a linear or branched, saturated or unsaturated, aliphatic hydrocarbon group having from 1 to 49 carbon atoms or a group:

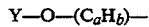
   $Y-O-(C_aH_b)-$ $R_1$ represents a linear or branched, saturated or unsaturated, aliphatic hydrocarbon group having from 8 to 28 carbon atoms;
   $R_2$ represents H, a phosphate, a sulphate, or a glucosyl:
   a is an integer from 7 to 50
   b is an integer from 10 to 100
   m is 0 or 1
   Y represents H or a $C_{14}-C_{22}$ fatty acid group having structure:

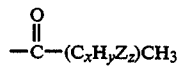

where
   z is —OH or an epoxy oxygen
   x is an integer of from 12 to 20
   y is an integer of from 20 to 40
   z is 0 or an integer of from 1 to 4; and (ii) from about 30 to about 95% by weight of a $C_6-C_{100}$ ester base functioning as a pharmaceutically acceptable carrier, said ester base comprising from about 1 to about 90% by weight of a material selected from the group consisting of $C_7-C_{60}$ neoalkanol ester, $C_{12}-C_{40}$ fatty glyceride ester alkoxylated with from 1 to 100 moles $C_2-C_3$ alkylene oxide per mole of glyceride and mixtures thereof; and (iii) from about 0.1 to about 20% by weight of glycerol monoisostearate as a coupling agent for solubilizing said ceramide within said base.

2. A cosmetic composition according to claim 1 further comprising from about 1 to about 50% by weight of a silicone.

3. A cosmetic composition according to claim 1 wherein the N-phytosphingosine-containing ceramide is Ceramide 3 having structure:

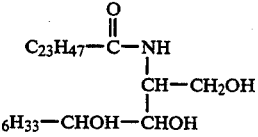

* * * * *